(12) United States Patent
Qian et al.

(10) Patent No.: US 9,131,691 B2
(45) Date of Patent: Sep. 15, 2015

(54) USE OF AMIDE COMPOUNDS FOR PREVENTING MARINE BIOFOULING

(75) Inventors: Peiyuan Qian, Hong Kong (CN); Xiangzhong Huang, Yunnan (CN); Ying Xu, Hong Kong (CN); Yu Zhang, Hong Kong (CN); Yue Him Wong, Hong Kong (CN); Yan Yin, Yunnan (CN); Zhuang Han, Hong Kong (CN)

(73) Assignees: The Hong Kong University of Science and Technology, Hong King (CN); Yunnan University of Natonalities, Yunnan (CN)

( * ) Notice: Subject to any disclaimer, the term of this patent is extended or adjusted under 35 U.S.C. 154(b) by 0 days.

(21) Appl. No.: 14/112,491

(22) PCT Filed: Apr. 17, 2012

(86) PCT No.: PCT/CN2012/000523
§ 371 (c)(1),
(2), (4) Date: Oct. 17, 2013

(87) PCT Pub. No.: WO2012/146055
PCT Pub. Date: Nov. 1, 2012

(65) Prior Publication Data
US 2014/0044810 A1    Feb. 13, 2014

(30) Foreign Application Priority Data
Apr. 27, 2011    (CN) .......................... 2011 1 0107418

(51) Int. Cl.
| | |
|---|---|
| A01N 65/00 | (2009.01) |
| A01N 43/40 | (2006.01) |
| A61K 36/00 | (2006.01) |
| A01N 43/30 | (2006.01) |
| C07D 317/60 | (2006.01) |
| B08B 17/02 | (2006.01) |
| C09D 5/16 | (2006.01) |
| B08B 17/04 | (2006.01) |
| A01N 65/08 | (2009.01) |

(52) U.S. Cl.
CPC ................ *A01N 43/40* (2013.01); *A01N 43/30* (2013.01); *A01N 65/08* (2013.01); *A61K 36/00* (2013.01); *B08B 17/02* (2013.01); *B08B 17/04* (2013.01); *C07D 317/60* (2013.01); *C09D 5/165* (2013.01); *C09D 5/1625* (2013.01)

(58) Field of Classification Search
CPC ...................................................... A61K 36/00
USPC .......................................................... 424/725
See application file for complete search history.

(56) References Cited

FOREIGN PATENT DOCUMENTS

JP    2001-207125 A    7/2001

OTHER PUBLICATIONS

Huang, X. et al. "Alkaloids and lignans from stems of *Piper betie*" *China Journal of Chinese Materia Medica*, Sep. 2010, 35(17):2285-2288.
Rao, V.R.S. et al. "Novel dimeric amide alkaloids from *Piper chaba* Hunter: isolation, cytotoxic activity, and their biomimetic synthesis" *Tetrahedron*, Jan. 2011, 67:1885-1892.
International Search Report in International Application No. PCT/CN2012/000523, filed Apr. 17, 2012.

*Primary Examiner* — Michael Meller
(74) *Attorney, Agent, or Firm* — Saliwanchik, Lloyd & Eisenschenk (57) ABSTRACT

Use of amide compounds represented by formula (I), for preventing or reducing settlement and/or fouling of marine fouling organisms on a surface of a submerged object is provided, wherein "-A-" has a formula —(CnH2(n-m))- which is either unsubstituted or substituted by one or more C1 to C4 alkyls, and wherein the formula —(CnH2(n-m))- represents a divalent alkyl, or a divalent alkenyl having one or more double bonds, n is 1 to 15, m is 0 to 4, and 2(n-m)=2, and R is selected from piperidinyl, pyrrolidinyl, isobutylamino, piperazinyl or morpholinyl. Amide compounds of formula (I), a category of antifouling compounds, can be either isolated from natural resources or synthesized, which are non-toxic and environmental-friendly.

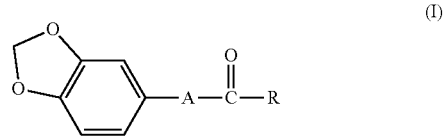

(I)

1 Claim, 7 Drawing Sheets

USE OF AMIDE COMPOUNDS FOR PREVENTING MARINE BIOFOULING

CROSS-REFERENCE TO RELATED APPLICATIONS

This application is the U.S. national stage application of International Patent Application No. PCT/CN2012/000523, filed Apr. 17, 2012, which claims priority to Chinese Application No. 201110107418.9, filed Apr. 27, 2011, the disclosures of each of which are incorporated herein by reference in their entirety.

CROSS REFERENCE

This application claims benefit from Chinese patent application number 201110107418.9, filed on 27 Apr. 2011, the content of which is hereby incorporated in its entirety by reference.

FIELD OF THE INVENTION

The present invention relates to use of amide compounds in the prevention of marine biofouling. Particularly, it relates to the use of the amide compounds in inhibition of settlement of marine fouling organisms. These amides were isolated from Piper plants such as *Piper betle* L. and *Piper szemaoense* C.

BACKGROUND OF THE INVENTION

Marine fouling organisms refer to the whole host of organisms that can attach to and grow on the hulls of boats and the surface of other submerged artificial structures.

There are more than 2000 reported biofoulers in the world, the most harmful ones of which include barnacles, oysters, mussels, tubeworms and bryozoans, etc. There are about 200 main biofoulers in Chinese coastal area. These fouling organisms can cause extensive damage to commercially-important marine structures, which is one of the most serious problems in maritime and aquaculture industries. They can increase frictional resistance on the hulls of ships, leading to consumption of more fuel to maintain a normal speed, cause marine machinery and instrument equipment failure, absorb the acoustic energy of sound waves and sequentially make acoustic instrument ineffective, accelerate the corrosion of the substrate (e.g., steel material, aluminum material etc.) surfaces, increase the cross-sectional area of stakes and columns of marine structures and hence the impact caused by waves and ocean currents, increase the weight of buoys, block seawater pipes, decrease water exchange through aquaculture net boxes, and other negative effects. It is estimated that governments and industry spend over US $6.5 billion annually to prevent and control marine biofouling.

The study of biofouling and antifouling technology has received widespread attention from different coastal countries and areas because of the importance in the military and economic area. Common strategies of preventing marine biofouling include chlorine release, electrolysis antifouling, ultrasound, impressed current, the use of radioactive material, submerged mechanical cleaning, coating marine antifouling paints and so on. Among these, coating antifouling paints is the most effective way because it is a mature technology using simple procedures and has broad application scope. However, it is crucial to discover suitable marine antifoulants in the development of marine antifouling paints. With the prohibited use of the toxic antifoulants such as organic arsenic compounds, organo-lead compounds, mercuric oxide, and dichlorodithenyltrichloroethane (DDT) after 1970s, organotins, represented by tributyltin (TBT), and cuprous oxide were effectively used to prevent marine biofouling as common anti-fouling agents. However, it has been discovered that TBT persists in water and sediments, killing marine organisms in addition to those attached to ship hulls since 1980s. High concentrations of TBT in shellfish on the coast of France caused the collapse of commercial shell fisheries in at least one area. TBT caused shell deformations in oysters and sex changes (imposex) in gastropod, and bioaccumulated in fish and mammals. These events and findings prompted the Marine Environment Protection Committee (MEPC) of the International Maritime Organization (IMO) to implement a ban on the application of TBT paints from Jan. 1, 2003, with the intent that no TBT paints will remain on vessels after 2008. At present, antifouling paints containing copper and its compounds (e.g., cuprous oxide) have gained dominance in the market. However copper can accumulate in ocean, especially in harbour and hence cause massive death of marine algae which will impact the food web in the marine environment. Therefore finally copper and its compounds used as antifoulants will be replaced.

In order to protect the marine environment, biologists and natural product chemists have industriously been searching for effective and environmentally friendly natural antifoulants from natural resources. Natural products have no or very low acute and chronic toxicity to marine organisms, can be easily and quickly degraded and thus fail to cause permanent accumulation in the marine environment, and are abundantly available from natural resources. So far, a number of natural products with antifouling activities have been discovered from extracts of natural resources such as marine plants and animals and terrestrial plants, including terpenoids, alkynes, polycyclic compound, Steroids, isothiocyanates, etc. Most of these natural products have obvious repellent action to marine fouling organisms, but cause little or no damage to the marine environment. Therefore, it is hopeful to obtain non-toxic, high-efficient, broad-spectrum, degradable natural antifoulants and thus replace the toxic antifoulants.

The present invention provides a number of environmentally-friendly, natural anti-fouling agents, compositions, and applications.

SUMMARY OF THE INVENTION

Objects of the present invention are to provide the use of amide compounds in the prevention of marine biofouling, the antifouling paint containing these amide compounds and its preparation method, and a method of using the paint for preventing the larval settlement and proliferation of marine fouling organisms on a surface of an object immersed in water.

To be specific, the present invention provides:

(1) Use of amide compounds represented by formula I, for preventing or reducing settlement and/or fouling of marine fouling organisms on a surface of a submerged object:

I wherein "-A-" has a formula —$(C_nH_{2(n-m)})$—, which is either unsubstituted or substituted by one or more $C_1$ to $C_4$ alkyls, and wherein the formula —(C$_n$H$_{2(n-m)}$)— represents a divalent alkyl, or a divalent alkenyl having one or more double bonds, n is 1 to 15, m is 0 to 4, and 2(n-m)≥2, and R is selected from piperidinyl, pyrrolidinyl, isobutylamino, piperazinyl or morpholinyl.

(2) The use according to (1), wherein n=4~12, m=1~3.

(3) The use according to (1), wherein the amide compounds comprise one or more compounds represented by formulas II~V:

II

III

IV, and

V (4) The use according to (3), wherein the one or more of the compounds represented by formulas II~V exist in a extract of Piper plants which was extracted with a solvent and are used in the form of the extract, and wherein the solvent comprises 70-95 vol % ethanol/water solution, 70-90 vol % methanol/water solution, or 50-70 vol % acetone/water solution, and wherein the Piper plants is *Piper betle* L. or *Piper szemaoense* C.

(5) The use according to any one of (1) to (4), wherein the marine fouling organisms are selected from one or more of barnacles, tubeworms and bryozoans.

(6) The use according to any one of (1) to (4), wherein the amide compounds can be blended as antifouling components into film-forming components, and are therefore made into antifouling coating material which can be used to inhibit the settlement and/or fouling of marine fouling organisms on the surface of the submerged object, and wherein the film-forming components comprise one or more of hydrolysable, soluble or insoluble resins.

(7) An antifouling coating for preventing or reducing settlement and/or fouling of marine fouling organisms on a surface of a submerged object, wherein the antifouling coating comprises film-forming components and antifouling components, and wherein the film-forming components comprise one or more of hydrolysable, soluble or insoluble resins, and the antifouling components comprise one or more of amide compounds represented by formula I:

I wherein "-A-" has a formula —(C$_n$H$_{2(n-m)}$)—, which is either unsubstituted or substituted by one or more C$_1$ to C$_4$ alkyls, and wherein the formula —(C$_n$H$_{2(n-m)}$)— represents a divalent alkyl, or a divalent alkenyl having one or more double bonds, n is 1 to 15, m is 0 to 4, and 2(n-m)≥2, and R is selected from piperidinyl, pyrrolidinyl, isobutylamino, piperazinyl or morpholinyl.

(8) The antifouling coating according to (7), wherein n=4~12, m=1~3.

(9) The antifouling coating according to (7), wherein the antifouling components comprises one or more compounds represented by formulas II~V:

II

III

IV, and

V (10) The antifouling coating according to (9), wherein the one or more of the compounds represented by formulas II~V exist in a extract of Piper plants which was extracted with a solvent and are used in the form of the extract, and wherein the solvent comprises 70-95 vol % ethanol/water solution, 70-90 vol % methanol/water solution, or 50-70 vol % acetone/water solution, and wherein the Piper plants is *Piper betle* L. or *Piper szemaoense* C.

(11) The antifouling coating according to any one of (7) to (10), wherein the marine fouling organisms are selected from one or more of barnacles, tubeworms and bryozoans.

(12) A method for preventing or reducing settlement and/or fouling of marine fouling organisms on a surface of a submerged object, which comprises painting the surface of the submerged object with the antifouling coating according to any one of (7) to (11).

The advantages of the invention are as follows: 1. The amide compounds mentioned in the invention are non-toxic, non-heavy-metal-based organic compounds from natural resources, which can be easily and quickly degraded and fail to cause permanent accumulation in the marine environment. Thus, they are all environmentally-friendly anti-fouling agents. They can effectively inhibit the settlement of fouling organisms but won't kill non-target organisms.

2. The amide compounds mentioned in the invention have good antifouling activities and a broad antifouling spectrum. They can also be lead compounds for future development of other antifouling compounds, antifouling coatings or other products.

3. The amide compounds mentioned in the invention can be easily prepared from the aforementioned Piper plants which are widely distributed in mainland China, and the content of these compounds is high in the Piper plants, especially, *P. betle* L. and *P. szemaoense* C.

4. The extraction and purification of the aforementioned amide compounds from piper plants can be easily performed with ordinary extraction and chromatographic techniques in a few steps, yielding high purity products. Thus the industrial production thereof is practical and can be easily realized.

DETAILED DESCRIPTION OF THE INVENTION

The following detailed description of particular embodiments of the invention should not be treated as a limit to the scope of the invention. Amendments and improvements based on the invention are also within the scope of the invention.

The amide compounds mentioned in the invention can be from or derived from natural resources, and they can also be synthesized.

The antifouling coating mentioned in the invention include but not limited to known antifouling coatings that contain both the film-forming components and one or more antifouling components or Piper plant extracts mentioned in the invention. For example, the coatings may be water-soluble bulk coatings, self-polishing copolymer antifouling coatings, non-adhesive coatings, low surface energy antifouling coatings, adhesive coatings, bionical antifouling coatings and natural antifouling coatings (ZHANG Donghui, ZHOU Li, SU Wei, and SUN Yan. Review on anti-fouling coatings. *Modern Paint and Finishing*. 2007, 10(5):27-29).

The content on of the antifouling components in the antifouling coatings or paints mentioned in the invention could be any value within the effective range. For example, based on the total weight of the film-forming components, the amount of the antifouling components could be 0.1 wt %~20 wt %, preferably 1 wt %~15 wt %.

The "effective range" mentioned in the invention is the content of the aforementioned antifouling components at which the antifouling effect of the components is prominent under certain conditions.

The film-forming components mentioned in the invention include but not limited to the film-forming components of the known antifouling paints used for preventing marine biofouling. These film-forming components may include hydrolysable, soluble and insoluble resins. For example, they can be glyptal resin, acrylic resin, chlorinated rubber resin, epoxy resin, silicone resin, polyester resin, polyurethane resin, fluoropolymer resin and so on.

The antifouling components mentioned in the invention include one or more of amide compounds represented by formula I:

I wherein "-A-" has a formula —$(C_nH_{2(n-m)})$—, which is either unsubstituted or substituted by one or more $C_1$ to $C_4$ alkyls, and wherein the formula —$(C_nH_{2(n-m)})$— represents a divalent alkyl, or a divalent alkenyl having one or more double bonds, n is 1 to 15, m is 0 to 4, and 2(n-m)≥2, and R is selected from piperidinyl, pyrrolidinyl, isobutylamino, piperazinyl or morpholinyl. The antifouling components mentioned in the invention may also include the extract which was extracted from Piper plants with solvents, such as organic solvents. The aforementioned organic solvents may be 70-95 vol % ethanol/water solution, 70-90 vol % methanol/water solution, or 50-70 vol % acetone/water solution.

There are around 2000 species belonging to the genus Piper in the Piperaceae family. Around 60 of them are distributed in but not limited to China, mostly in Taiwan, Yunnan, Hainan and the south part of Guangxi. The *Piper betle* L. is one of them. It has been used as herbal medicine to cure worm and to treat bad breathing caused by cold or asthma. It has also been used to treat rheumatic ache, stomache caused by cold, cyesedema, and skin itches. *Piper szemaoense* C. is another kind of piper plants. It is mostly distributed in the Yunnan Province of mainland China. It has been used as herbal medicine to treat cold, rheumatic ache, stomache, menstrual disorder, traumatic injury and catagma. The major chemical components of Piper plants include alkaloids, lignanoids, flavone, phenylpropanoids, and volatile oils. Pharmacology studies have shown that these plants have analgesic, anti-inflammation, antibiotic, anti-oxidation, anti-depression, and anti-tumor effects. Most of the studies relative to Piper plants have been focusing on the amide-like alkaloids and lignanoids, including their pharmacology.

The inventors of the invention found that the extract of a solvent (e.g., 70 vol % acetone/water) from Piper plants such as *P. betle* L. and *P. szemaoense* C. showed strong anti-fouling effects (e.g., anti-settlement activity against *B. amphitrite larvae*) in bioassays. Based on the bioassays with *B. amphitrite*, the amide compounds with significant antifouling bioactivity were isolated from the extract from Piper plants by column chromatography, including those using Sephadex LH-20, Rp-18 silica, and common silica columns. These amides have linear structures with two head groups on each end, linked by long chain acyls or enoyls. Specifically:

1) The chemical group located on one end of the amides is 3,4-methylenedioxyphenyl group as shown below:

2) The chemical groups located on the two ends of the amides are linked by long chain acyls or enoyls. The chain length is 1~15 carbons;
3) The chemical group located on the other end of the amides is a polar group containing nitrogen.

The structure of these amide compounds may be represented by formula I:

I wherein "-A-" has a formula —$(C_nH_{2(n-m)})$—, which is either unsubstituted or substituted by one or more $C_1$ to $C_4$ alkyls, and wherein the formula —$(C_nH_{2(n-m)})$— represents a divalent alkyl, or a divalent alkenyl having one or more double bonds, n is 1 to 15, m is 0 to 4, and $2(n-m) \geq 2$. Preferably, n=4~12, m=1~3. R in formula I represents polar group with nitrogen. As the particular non-limiting embodiments of the present invention, R may be one of the groups as shown below:

piperidinyl    pyrrolidinyl    isobutylamino group piperazinyl    morpholinyl

As particular non-limiting embodiments of the present invention, the following four Compounds 1-4 are representatives of the amide compounds of the present invention:

Compound 1 (piperoleine B): 1-[1-oxo-9-(3',4'-methylenedioxyphenyl)-8E-nonenyl]-piperine, having the chemical structure of

Compound 2 (piperine): 1-[1-oxo-5-(3',4'-methylenedioxyphenyl)-2,4-pentadienoyl]-piperidine, having the chemical structure of Compound 3 (piperdardine): 1-[1-oxo-7-(3',4'-methylenedioxyphenyl)-2E,4E-heptadienyl]-piperine, having the chemical structure of Compound 4 (guineensine): (2E,4E,12E)-N-isobutyl-13-(3',4'-methyl enedioxyphenyl)-tridecatrienamide, having the chemical structure of The target organisms which can be inhibited by the antifouling amide compounds mentioned in the invention include but not limited to barnacles, tubeworms and bryozoans. Preferably, these amide compounds may at least inhibit settlement of one or more of barnacles, tubeworms and bryozoans. Preferably, these amide compounds may inhibit larvae settlement of barnacles, tubeworms and bryozoans.

The four amides (piperoleine B, piperine, piperdardine and guineensine) were tested for their abilities to inhibit larvae settlement of three typical marine fouling organisms, the barnacle B. amphitrite, the polychaete H. elegans and the bryozoan B. neritina. The calculated $EC_{50}$ of the four amides against the larval settlement of B. amphitrite cyprids were 1.1±0.3 µg/ml, 1.4±0.6 µg/ml, 4.2±1.3 µg/ml, and 16.6±2.9 µg/ml, respectively. Their $EC_{50}$ against the H. elegans larvae were 1.0±0.4 µg/ml, 1.3±0.8 µg/ml, 7.3±1.6 µg/ml, and >20.0 µg/ml, respectively, and their $EC_{50}$ against the B. neritina larvae were 0.7±0.2 µg/ml, 1.6±0.7 µg/ml, 8.5±2.1 µg/ml, and 5.7±1.5 µg/ml, respectively. The aforementioned results showed the four amides have outstanding activities against the marine fouling organisms, among which piperoleine B and piperine have stronger inhibitory activities against larvae of these three fouling organisms and their $EC_{50}$ values on these three species were less than 2.0 µg/ml, which indicated these two compounds have broad-spectrum properties in anti-larvae settlement of marine fouling organisms.

According to Avelin et al. (Mary A., Mary V., Rittschof D., Nagabhushanam R. Bacterial-barnacle interaction: potential of using juncellins and antibiotics to alter structure of bacterial communities. J Chem. Ecol. 1993,19(10):2155-2167), an antifouling compound with a $LC_{50}/EC_{50}$ value of higher than 10 was regarded as a non-toxic compound. The $LC_{50}/EC_{50}$ ratios of all these four amides were higher than 10 in a bioassay against these three species, which indicated that these four amides are non-toxic or low-toxic antifouling compounds.

Moreover, the present invention provides the preparation method of the aforementioned amide compounds. This method is related to the preparation of these amide compounds from Piper plants such as P. betle L. and P. szemaoense C. Preferably, piperoleine B, piperine, piperdardine and guineensine were prepared from the roots, stems, leave and fruits of P. betle L. Preferably, This method includes the following steps:

(1) The stems of P. betle L. were air-dried and crushed into pieces or powder;

(2) The pieces or powder of the stems from P. betle L. was soaked and extracted with solvents (e.g., organic solvents) to obtain a extraction liquid;

(3) The aforementioned extraction liquid was filtered and concentrated in a speed-vac to get a black mass;

(4) The aforementioned black mass was suspended in water, and then sequentially partitioned with petroleum ether, ethyl acetate and n-butanol, which were concentrated to give a petroleum ether extract, ethyl acetate extract and n-butanol extract, successively;

(5) The ethyl acetate extract was separated into ten fractions (Fr. 1~Fr. 10) on a silica gel column using step gradient elution with petroleum ether-ethyl acetate (10:0~2:1, v/v) and ethyl acetate-methanol (20:1~0:1, v/v);

(6) The Fr. 2 was purified by Sephadex LH-20 column using methanol as a solvent, and then was subjected to silica gel column eluted with petroleum ether-acetone (16:1~5:1, v/v) to obtain Fr. 2-1~Fr. 2-5. The Fr. 2-3 was subjected to repeated column chromatography on Rp-18 silica and eluted with methanol-$H_2O$ (65:35~85:15, v/v) to obtain Compounds 1, 2 and 3. The Fr. 2-2 was applied to RP-18 silica gel column and eluted with methanol-$H_2O$ (65:35~90:10, v/v) to afford Compound 4.

The solvent for extraction in step 2 may be 70-95 vol % ethanol/water solution, 70-90 vol % methanol/water solution, or 50-70 vol % acetone/water solution. And a hot reflux extraction is used. The time of the hot reflux extraction is 2 hours each time and the hot reflux extraction was preferably repeated three times.

The present invention also provides the preparation method of the antifouling coatings or paints, comprising the following steps: (1) providing the antifouling components; (2) mixing the antifouling components obtained by step (1) with film-forming components to get the antifouling paints, in which antifouling components obtained by step (1) may be the compounds represented by formula I and also may be obtained from the following method: extracting Piper plants with the aforementioned solvents to obtain an extraction liquid; filtering the extraction liquid and concentrating the filtered liquid in a speed-vac to get a black mass. This black mass can be used as the antifouling components.

In addition, the present invention provides the use of the amide compounds in the preparation of antifouling paints. These compounds with antifouling activities mentioned in the invention have the effect of preventing biofouling. Therefore, these compounds with antifouling activities can be used to prepare high-efficient antifouling paints.

At the same time, the present invention provides a method of preventing marine biofouling, comprising: painting the surface of a submerged object using the antifouling paints of the invention.

The submerged objects mentioned in the invention include but not limited to drain pipe, the part of a ship's hull below water line, boat propeller, net cage for breeding fish, underwater structures of docks and offshore oil platforms, submarine mine, buoy, submarine cable, coastal cooling pipe of power plants and so on.

EXAMPLES

The invention will be further described with the following Examples so as to be fully understood, but it should be understood that the scope of the invention is not limited by the same.

Example 1

The Inhibitory Effect of the Extract of Piper Plants on Larval Settlement of the Barnacle B. amphitrite The raw material sources: The dry stems of P. betle L. and P. szemaoense C. mentioned in the invention were collected from Yunnan Province in China, in November 2007. A voucher specimen (No. 20071124) was deposited in School of Chemistry and Biotechnology, Yunnan University of Nationalities, China, and was identified by Prof. Shaobin Ma, Department of Biology, Yunnan University.

The extraction preparation of P. betle L. and P. szemaoense C.: The stems of P. betle L. and P. szemaoense C. were air-dried and crushed into powder (diameter 0.1-0.5 cm), which was extracted with 70 vol % acetone/water solution three times under reflux for 2 h each time. The crude extract was filtered and concentrated in a speed-vac to get a black mass.

The extracts of P. betle L. and P. szemaoense C. were tested for their abilities to inhibit larvae settlement of the barnacle B. Amphitrite, using an experimental model of inhibition of larvae settlement of B. Amphitrite cyprids (Xu Y., He H. P., Qian P. Y, et al. Potent antifouling compounds produced by marine streptomyces. *Bioresource Technology.* 2010, 101(4): 1331-1336). Adult brood stocks of B. amphitrite Darwin were collected from Pak Sha Wan, Hong Kong (22° 19'N, 114° 16'E). They were kept in sea water at room temperature in lab under light illumination to induce the release of nauplii larvae. These newly released nauplii were reared to the cyprid stage on a diet of Chaetoceros gracilis Schutt at 28° C. for about 3 days until they developed into cyprids, which were ready to settle. The cyprids were collected using a 120 μm mesh sieve. Each sample of the exacts was dissolved in a small amount of DMSO and then transferred into filtered seawater to make up the test solution with a known concentration. About fifteen (15±3) cyprids per well were incubated in the dark for 48 h in a 24-well plate filled with 1 ml testing solutions per well. The numbers of the settled and swimming larvae were counted under a dissecting microscope. Three replicates were run for each sample. The $EC_{50}$ was calculated as the concentration where 50% of the larval population was inhibited to settle as compared to the control, while $LC_{50}$ was calculated as the concentration where 50% of the larval population was dead. The experiment was performed in quadruplicate.

The results showed that each extract of P. betle L. and P. szemaoense C. had significant inhibitory activities against larvae of B. Amphitrite (Table 1).

TABLE 1 the inhibitory effect of each extract of P. betle L. and P. szemaoense C. on larval settlement of B. amphitrite.

| Sample | The rate of settlement (%) | |
| --- | --- | --- |
| | 50 μg/ml | 10 μg/ml |
| the extract of P. betle L. | 0.0% | 28.1 ± 2.2% |
| the extract of P. szemaoense C. | 6.6 ± 1.3% | 52.7 ± 2.7% | n = 4

Comparative Example 1

The stems of P. betle L. and P. szemaoense C. were air-dried and crushed into powder (diameter: less than 100 μm). The powders of P. betle L. and P. szemaoense C. were directly used to repeat the aforementioned experiment. The results showed that the powders of each of the two plants had no significant inhibitory activities against larvae of B. Amphitrite at the concentration of 50 μg/ml or below (Table 2), and also showed that the inhibitory activities of the powders of each of the two plants against larvae of B. Amphitrite were lower than those of their extracts.

TABLE 2 the inhibitory effect of the powders of P. betle L. and P. szemaoense C. on larval settlement of B. amphitrite.

| Sample | The rate of settlement (%) | |
| --- | --- | --- |
| | 50 μg/ml | 10 μg/ml |
| the powder of P. betle L. | 92.5 ± 2.9% | 98.2 ± 1.8% |
| the powder of P. szemaoense C. | 94.0 ± 2.7% | 97.6 ± 2.1% | n = 4

Example 2

Further Experiments on P. betle L

There have been previously few reports about studies on the chemical components of P. betle L. Moreover, the extract of P. betle L. had better inhibitory activity against larvae of B. Amphitrite than the extract of P. szemaoense C. Thus, P. betle L. was selected for further experiments. This doesn't indicate that P. szemaoense C and other Piper plants have no inhibitory activities against fouling organisms.

A 95 vol % ethanol/water solution and 90 vol % methanol/water solution were used as extract solvents for repeating the Example 1, respectively. The results showed that the inhibitory activities of both the 95 vol % ethanol/water extract from P. betle L. and 90 vol % methanol/water extract from P. betle L. in the bioassay with B. Amphitrite were as significant as those of the 70 vol % acetone/water extract (Table 3), and also showed that the inhibitory activities of the powders of each of the two plants against larvae of B. Amphitrite were lower than those of their extracts. So the antifouling components of P. betle L. also can be extracted with different concentration of ethanol/water or methanol/water solutions as extract solvents.

TABLE 3 the inhibitory effect of the different solvent extracts of P. betle L. on larval settlement of B. amphitrite.

| Sample | The rate of settlement (%) | |
| --- | --- | --- |
| | 50 μg/ml | 10 μg/ml |
| 70% acetone/water extract | 0.0% | 28.1 ± 2.2% |
| 95% ethanol/water extract | 0.0% | 37.5 ± 3.1% |
| 90% methanol/water extract | 0.0% | 32.7 ± 3.7% | n = 4

Example 3

Isolation and Identification of Antifouling Compounds from P. betle L

The stems of P. betle L. were air-dried and crushed into powder (diameter 0.1-0.5 cm), which was extracted with an organic solvent to obtain the crude extract. The organic solvent is a 70 vol % acetone/water solution. The powder of Piper betle stem was extracted with solvent three times under reflux for 2 h each time. The crude extract was filtered and concentrated in a speed-vac to get a black mass. The black mass was suspended in water in a ratio of 300 ml water per 100 g black mass, and then sequentially partitioned with petroleum ether ($V_{petroleum\ ether}/V_{water}=1:1$), ethyl acetate ($V_{ethyl\ acetate}/V_{water}=1:1$) and n-butanol ($V_{n-butanol}/V_{water}=1:$ 1), which were concentrated to give the petroleum ether extract (36 g), ethyl acetate extract (170 g) and n-butanol extract (50 g), successively. Part of the ethyl acetate extract (56 g) was separated into ten fractions (Fr. 1~Fr. 10) on a silica gel column (200-300 mesh) using step gradient elution with petroleum ether-ethyl acetate (10:0~2:1, v/v) and ethyl acetate-methanol (20:1~0:1, v/v). In the process of separation, the silica gel column was eluted with petroleum ether-EtOAC (10:1, v/v) to afford Fr. 1. Then the silica gel column was eluted with petroleum ether-EtOAC (4:1, v/v) to obtain Fr. 2.

Figure 1:
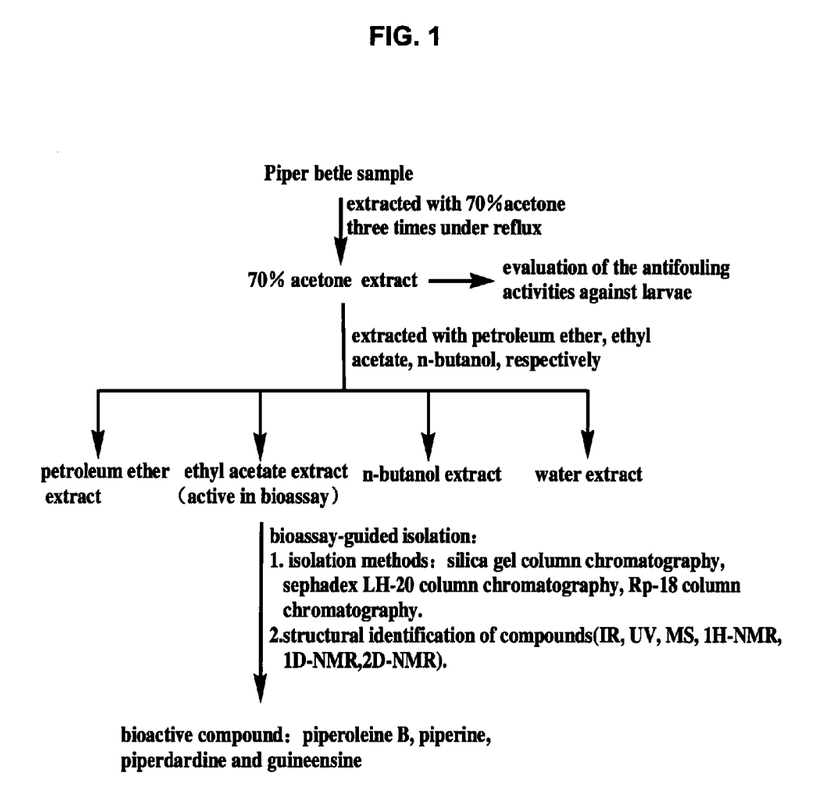
FIG. 1 is a flowchart of the isolation of the four (4) anti-fouling amide compounds from *Piper betle*.
Figure 2:
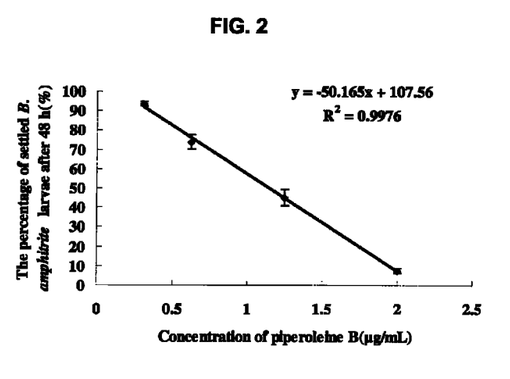
FIG. 2 shows the inhibitory effect of piperoleine B on larval settlement of the barnacle *Balanus amphitrite*. The results are presented as the mean±standard deviation of at least three replicates (n=3)
Figure 3:
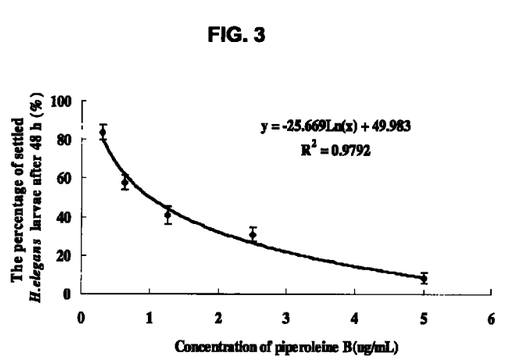
FIG. 3 shows the inhibitory effect of piperoleine B on larval settlement of the *Hydroides elegans*. The results are presented as the mean±standard deviation of at least three replicates (n=3)
Figure 4:
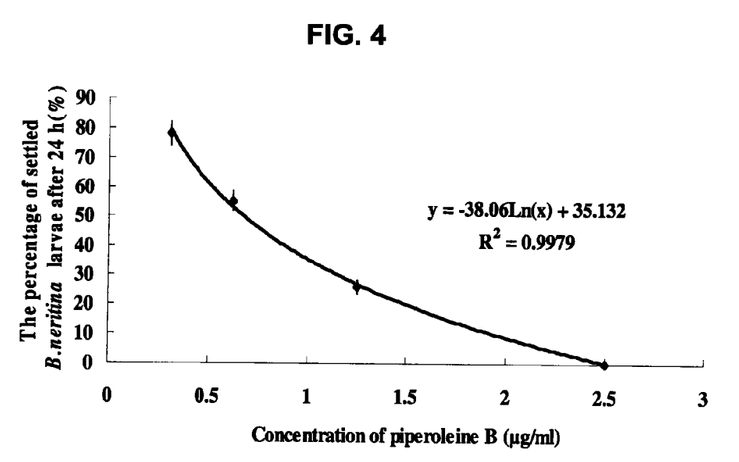
FIG. 4 shows the inhibitory effect of piperoleine B on larval settlement of the *Bugula neritina*. The results are presented as the mean±standard deviation of at least three replicates (n=3)
Figure 5:
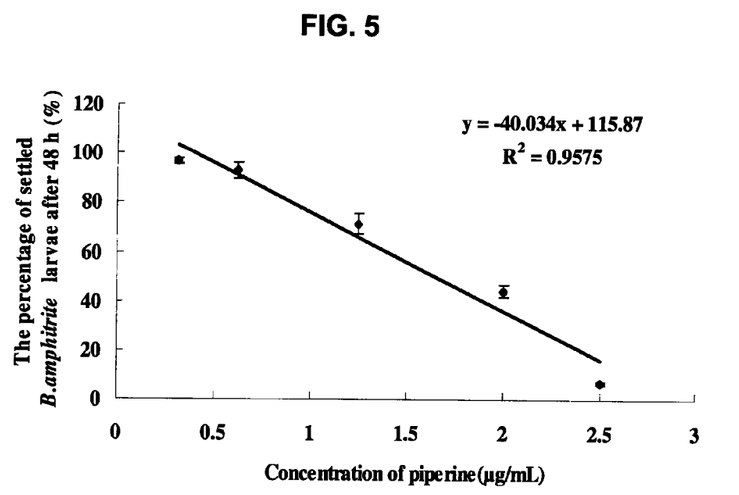
FIG. 5 shows the inhibitory effect of piperine on larval settlement of the barnacle *Balanus amphitrite*. The results are presented as the mean±standard deviation of at least three replicates (n=3)
Figure 6:
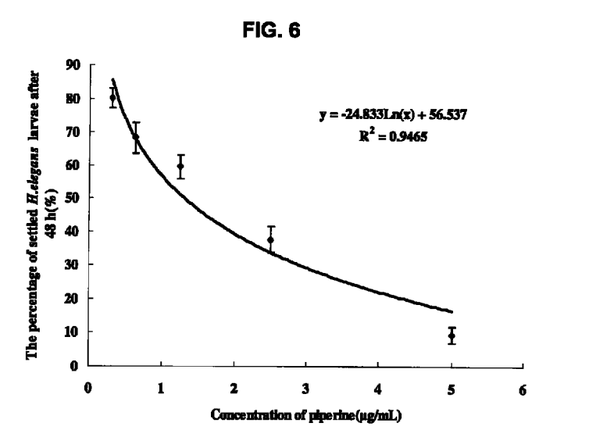
FIG. 6 shows the inhibitory effect of piperine on larval settlement of the *Hydroides elegans*. The results are presented as the mean±standard deviation of at least three replicates (n=3)
Figure 7:
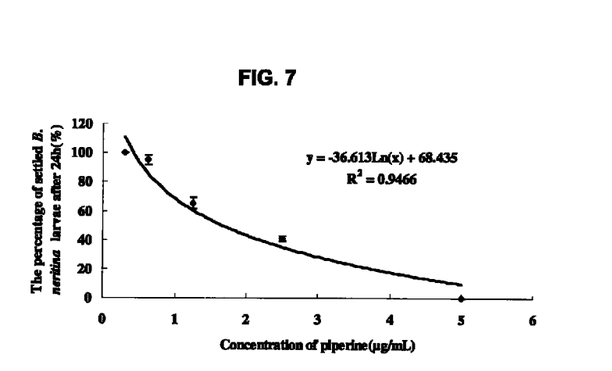
FIG. 7 shows the inhibitory effect of piperine on larval settlement of the *Bugula neritina*. The results are presented as the mean±standard deviation of at least three replicates (n=3)
Figure 8:
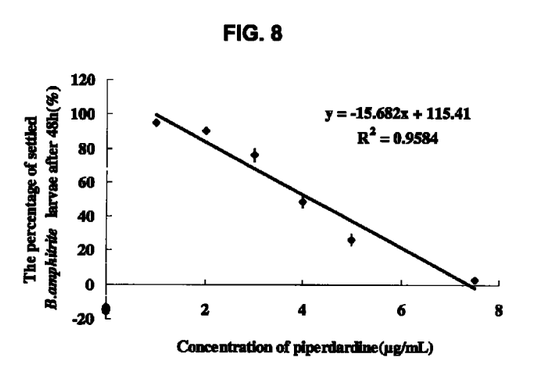
FIG. 8 shows the inhibitory effect of piperdardine on larval settlement of the barnacle *Balanus amphitrite*. The results are presented as the mean±standard deviation of at least three replicates (n=3)
Figure 9:
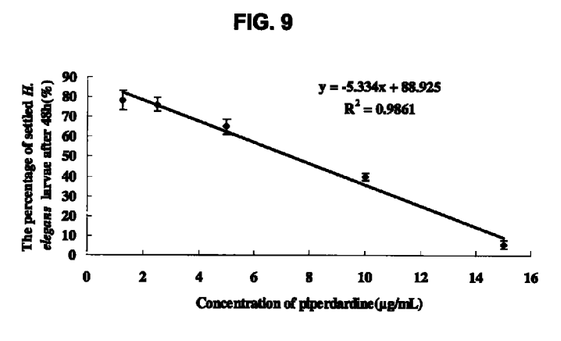
FIG. 9 shows the inhibitory effect of piperdardine on larval settlement of the *Hydroides elegans*. The results are presented as the mean±standard deviation of at least three replicates (n=3)
Figure 10:
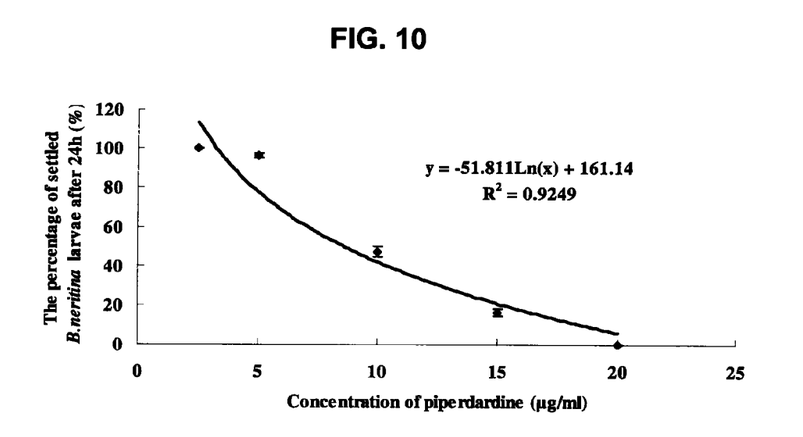
FIG. 10 shows the inhibitory effect of piperdardine on larval settlement of the *Bugula neritina*. The results are presented as the mean±standard deviation of at least three replicates (n=3)
Figure 11:
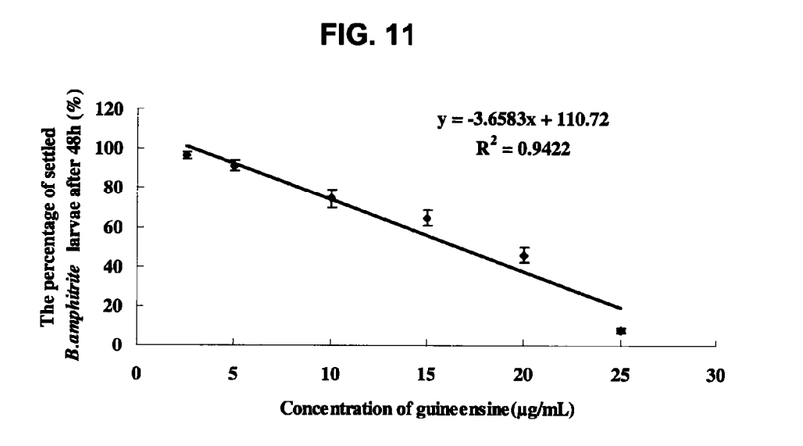
FIG. 11 shows the inhibitory effect of guineensine on larval settlement of the barnacle *Balanus amphitrite*. The results are presented as the mean±standard deviation of at least three replicates (n=3)
Figure 12:
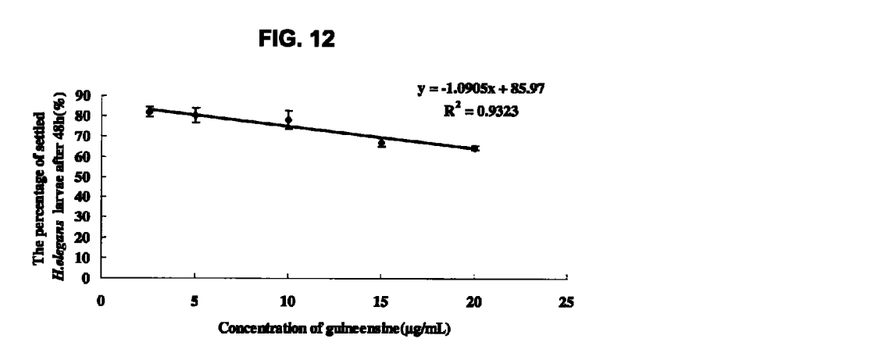
FIG. 12 shows the inhibitory effect of guineensine on larval settlement of the *Hydroides elegans*. The results are presented as the mean±standard deviation of at least three replicates (n=3)
Figure 13:
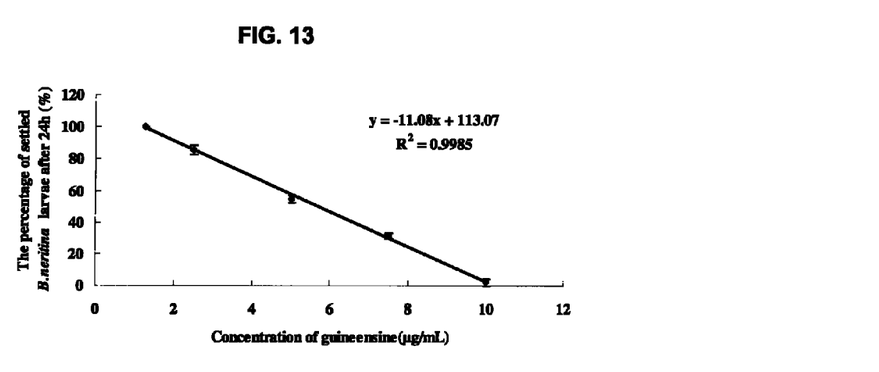
FIG. 13 shows the inhibitory effect of guineensine on larval settlement of the *Bugula neritina*. The results are presented as the mean±standard deviation of at least three replicates (n=3).

The Fr. 2 (8.5 g) was purified by Sephadex LH-20 column using methanol as a solvent, and then was subjected to silica gel column eluted with petroleum ether-acetone (16:1~5:1, v/v) to obtain Fr. 2-1~Fr. 2-5. Specifically, Fr. 2-1 was obtained by eluting the silica gel column with petroleum ether-acetone (16:1, v/v), Fr. 2-2 was obtained by eluting the silica gel column with petroleum ether-acetone (11:1, v/v), and Fr. 2-3 was obtained by eluting the silica gel column with petroleum ether-acetone (7:1, v/v). Next, Fr. 2-3 (5.52 g) was subjected to repeated column chromatography on Rp-18 silica and eluted with methanol-$H_2O$ (65:35~85:15, v/v) to obtain Compounds 1, 2 and 3. Fr. 2-2 (2.17 g) was applied to RP-18 silica gel column and eluted with methanol-$H_2O$ (65:35~90:10, v/v) to afford Compound 4. FIG. 1 shows the flow of separation and identification of antifouling constituents from the stem of P. betle L.

The structures of these compounds were identified based on analysis with NMR ($^1$H NMR, $^{13}$C NMR, DEPT and COSY HSQC, HMBC), positive ESI-MS, and IR spectroscopy. The detailed data are listed as following:

Compound 1 (piperoleine B): 1-[1-oxo-9-(3',4'-methylenedioxyphenyl)-8E-nonenyl]-piperine. Light yellow, oily, bismuth potassium iodide positive. ESI-MS m/z: 344 [M+H]$^+$, formula $C_{21}H_{29}NO_3$, IR (KBr) cm$^{-1}$: 1636, 1241, 1032, 963, 925; $^1$H NMR (500 MHz, CDCl$_3$) δ: 2.16 (2H, t, J=7.5, H-2), 1.30~1.62 (8H, m, H-3~6), 2.03 (2H, m, H-7), 6.01 (1H, dt, J=15.0, 6.5 Hz, H-8), 6.05 (1H, d, J=15.0 Hz, H-9), 3.61 (2H, br.s, H-1'), 1.48~1.60 (2H, m, H-2'), 1.61~1.70 (2H, m, H-3'), 1.48~1.60 (2H, m, H-4'), 3.48 (2H, br. s, H-5'), 6.88 (1H, s, H-2"), 6.28 (2H, d, J=8.0 Hz, H-5"), 6.73 (2H, d, J=8.0 Hz, H-6"), 5.91 (2H, s, —OCH$_2$O—). $^{13}$C NMR (125 MHz, CDCl$_3$) δ: 172.0 (C-1), 33.8 (C-2), 29.7 (C-3), 29.4 (C-4), 28.1 (C-5), 29.7 (C-6), 33.2 (C-7), 129.7 (C-8), 130.4 (C-9), 47.2 (C-1'), 26.4 (C-2'), 25.0 (C-3'), 26.0 (C-4'), 43.1 (C-5'), 132.7 (C-1"), 105.8 (C-2"), 148.3 (C-3"), 147.0 (C-4"), 108.6 (C-5"), 120.6 (C-6"), 101.3 (—OCH$_2$O—). Structure:

Compound 2 (piperine): 1-[1-oxo-5-(3',4'-methylenedioxyphenyl)-2,4-pentadienoyl]-piperidine. White needle-like crystal, Bismuth potassium iodide positive. ESI-MS m/z: 286 [M+H]$^+$, formula $C_{17}H_{19}NO_3$. IR (KBr) cm$^{-1}$: 2940, 1630, 1610, 1586, 1494, 834, 808, 610; $^1$H NMR (500 MHz, CDCl$_3$) δ: 6.43 (1H, d, J=14.0 Hz, H-2), 7.39 (1H, m, H-3), 6.69~6.74 (2H, m, H-4, 5), 3.52 (2H, br.s, H-1'), 1.58 (2H, m, H-2'), 1.65 (2H, m, H-3'), 1.58 (2H, m, H-4'), 3.62 (2H, br. s, H-5'), 6.97 (1H, s, H-2"), 6.88 (1H, dd, J=1.5, 7.5 Hz, H-6"), 6.77 (1H, d, J=7.5 Hz, H-5"), 5.96 (2H, s, —OCH$_2$O—); $^{13}$C NMR (125 MHz, CDCl$_3$) δ: 166.8 (C-1), 120.5 (C-2), 142.8 (C-3), 125.8 (C-4), 138.6 (C-5), 47.3 (C-1'), 27.1 (C-2'), 25.1 (C-3'), 26.0 (C-4'), 43.6 (C-5'), 131.5 (C-1"), 106.1 (C-2"), 148.6 (C-3"), 148.5 (C-4"), 108.9 (C-5"), 122.9 (C-6"), 101.7 (—OCH$_2$O—). Structure:

Compound 3 (piperdardine): 1-[1-oxo-7-(3',4'-methylenedioxyphenyl)-2E,4E-heptadienyl]-piperine. Light yellow, oily, bismuth potassium iodide positive. ESI-MS m/z: 314 [M+H]$^+$, formula $C_{19}H_{23}NO_3$. IR (KBr) cm$^{-1}$: 2931, 2855, 1621, 1489, 1442, 1248; $^1$H NMR (500 MHz, CDCl$_3$) δ: 6.25 (1H, d, J=15.0 Hz, H-2), 7.20 (1H, dd, J=15.0, 11.0 Hz, H-3), 6.16 (1H, dd, J=15.0, 11.0 Hz, H-4), 6.05 (1H, dt, J=15.0, 7.0 Hz, H-5), 2.41 (2H, dt, J=7.0, 7.5 Hz, H-6), 2.65 (2H, J=7.5 Hz, H-7), 3.46 (2H, br.s, H-2'), 1.43~1.59 (2H, m, H-3'), 1.60~1.69 (2H, m, H-4'), 1.43~1.59 (2H, m, H-5'), 3.60 (2H, br. s, H-6'), 6.65 (1H, s, H-2"), 6.59 (1H, dd, J=1.5, 8.0 Hz, H-5"), 6.69 (1H, d, J=8.0 Hz, H-6"), 5.93 (2H, s, —OCH$_2$O—); $^{13}$C NMR (125 MHz, CDCl$_3$) δ: 166.5 (C-1), 120.1 (C-2), 143.2 (C-3), 130.1 (C-4), 142.5 (C-5), 35.5 (C-6), 35.6 (C-7), 47.3 (C-1'), 27.19 (C-2'), 25.0 (C-3'), 26.1 (C-4'), 43.6 (C-5'), 135.8 (C-1"), 108.5 (C-2"), 148.6 (C-3"), 147.0 (C-4"), 106.6 (C-5"), 122.4 (C-6"), 101.3 (—OCH$_2$O—). Structure:

Compound 4 (guineensine): (2E,4E,12E)-N-isobutyl-13-(3',4'-methyl enedioxyphenyl)-tridecatrienamide. White needle-like crystal. Bismuth potassium iodide positive. ESI-MS m/z: 384 [M+H]$^+$, formula $C_{24}H_{32}NO_3$. IR (KBr) cm$^{-1}$: 3444~3305 (NH), 3090, 2927, 2874, 1656 (C=O), 1493, 1257, 1046; $^1$H NMR (500 MHz, CDCl$_3$) δ: 5.74 (1H, d, J=15.0 Hz, H-2), 7.21 (1H, dd, J=15.0, 10.0 Hz, H-3), 6.14 (2H, dd, J=15.0, 10.0 Hz, H-4, 13), 6.09 (2H, dt, J=15.6, 6.5 Hz, H-5, 12), 2.15 (4H, m, H-6, 11), 1.42 (8H, m, H-7~10), 6.89 (1H, s, H-2"), 6.73~6.89 (2H, s, H-5", 6"), 3.16 (2H, t, J=6.5, H-1'), 1.81 (1H, m, H-2'), 0.92 (6H, d, J=7.0, H-3', 4'), 5.57 (1H, br, s, N—H), 5.92 (2H, s, —OCH$_2$O—); $^{13}$C NMR (125 MHz, CDCl$_3$) δ: 166.8 (C-1), 122.2 (C-2), 141.6 (C-3), 129.8 (C-4, 13), 143.4 (C-5), 33.3 (C-6, 11), 29.4 (C-7, 9), 29.7 (C-8, 10), 128.3 (C-12), 47.3 (C-1'), 29.0 (C-2'), 20.5 (C-3', 4'), 132.7 (C-1"), 105.8 (C-2"), 148.3 (C-3"), 147.0 (C-4"), 108.6 (C-5"), 120.6 (C-6"), 101.3 (—OCH$_2$O—). Structure:

Example 4

The Anti-Settlement Activity of the Aforementioned Amide Compounds 1-4 were Evaluated by Inhibitory Assay Using the Competent Larvae of B. amphitrite Darwin The four amide compounds were tested for their abilities to inhibit larvae settlement of the barnacle B. Amphitrite, using an experimental model of inhibition of larvae settlement of B. Amphitrite cyprids (Xu Y., He H. P., Qian P. Y., et al. Potent antifouling compounds produced by marine streptomyces. Bioresource Technology. 2010, 101(4):1331-1336). Adult brood stocks of B. amphitrite Darwin were collected from Pak Sha Wan, Hong Kong (22° 19'N, 114° 16'E). They were kept in sea water at room temperature in lab under light illumination to induce the release of nauplii larvae. These newly released nauplii were reared to the cyprid stage on a diet of Chaetoceros gracilis Schutt at 28° C. for about 3 days until they developed into cyprids, which were ready to settle. The cyprids were collected using a 120 μm mesh sieve. Each compound sample was dissolved in a small amount of DMSO and then transferred into filtered seawater to make up the test solution with a known concentration. About fifteen (15±3) cyprids per well were incubated in the dark for 48 h in a 24-well plate filled with 1 ml testing solutions per well. The numbers of the settled and swimming larvae were counted under a dissecting microscope. Three replicates were run for each sample. The $EC_{50}$ was calculated as the concentration where 50% of the larval population was inhibited to settle as compared to the control, while $LC_{50}$ was calculated as the concentration where 50% of the larval population was dead. The experiment was performed in quadruplicate. The experiment results of the inhibitory effect of the four Compounds 1-4 on larvae settlement of the barnacle B. Amphitrite were shown in FIGS. 2, 5, 8, and 11, respectively.

The results showed that the four amides all had significant inhibitory activities against larvae of B. Amphitrite (Table 4), among which piperoleine B and piperine had stronger inhibitory activities against larvae of the fouling organism than the other two. According to Avelin et al. (Mary A., Mary V., Rittschof D., Nagabhushanam R. Bacterial-barnacle interaction: potential of using juncellins and antibiotics to alter structure of bacterial communities. J Chem. Ecol. 1993,19 (10):2155-2167), an antifouling compound with the $LC_{50}/EC_{50}$ value of higher than 10 was regarded as a non-toxic compound. All these four amides had the $LC_{50}/EC_{50}$ values of higher than 10 in the bioassay against this species, which revealed that they are non-toxic or low-toxic antifouling compounds.

TABLE 4 the inhibitory effect of piperoleine B, piperine, piperdardine and guineensine on larval settlement of B. amphitrite.

| No. | Sample Name | $EC_{50}$ (μg/ml) | $LC_{50}$ (μg/ml) | $LC_{50}/EC_{50}$ |
|---|---|---|---|---|
| 1 | piperoleine B | 1.1 ± 0.3 | >100 | >86.9 |
| 2 | piperine | 1.4 ± 0.6 | >100 | >71.4 |
| 3 | piperdardine | 4.2 ± 1.3 | >100 | >24.0 |
| 4 | guineensine | 16.6 ± 2.9 | >200 | >12.1 | n = 4, p < 0.01

Example 5

The Anti-Settlement Activity of the Aforementioned Amide Compounds (1-4) were Evaluated by Inhibitory Assay Using the Competent Larvae of H. elegans The four amide compounds were tested for their abilities to inhibit larvae settlement of the H. elegans, using an experimental model of inhibition of larvae settlement H. elegans (Zhang Y., Xiao K., Qian P. Y., et al. 2D gel-based multiplexed proteomic analysis during larval development and metamorphosis of the biofouling polychaete tubeworm Hydroides elegans. Journal of proteome research. 2010, 9(9), 4851-4860). Adults of H. elegans were collected from Yung Shue O, Hong Kong (22° 25'N, 114° 16'E). The H. elegans larvae were reared according to Qian and Pechenik (Bryan P. J., Qian P. Y., Kreider J. L.; Chia F. S. Induction of larval settlement and metamorphosis by pharmacological and conspecific associated compounds in the serpulid polychaete Hydroides elegans. Marine ecology progress series. 1997, 146: 81-90; Qiu, J. W.; Qian, P. Y. Combined effects of salinity, temperature and food on early development of the polychaete Hydroides elegans. Marine ecology progress series. 1997, 152: 79-88). Briefly, they were reared for 4 days until they reach the settlement-competent stage on a diet of chrysophyte Isochrysis galbana under an aerated condition and a 15 h light/9 h dark photoperied at 25° C. Because the attachment of H. elegans larvae requires to be induced by marine biofilm (Carpizo-Ituarte and Hadfield 1998), 24-well plates were suspended in laboratory tanks supplied with running seawater for 6 days until each well of every plate had accumulated sufficient biofilm. About fifteen (15±3) competent larvae were added to each biofilmed well of a plate containing 1.0 mL test solution containing samples at known concentrations. The 24-well plates were incubated at 28° C. for 48 h under a 15 h light/9 h dark photoperied. The percentage of larvae settlement and larvae mortality was determined by counting the settled, live individuals under a dissecting microscope. Three replicates were run for each sample. The $EC_{50}$ was calculated as the concentration where 50% of the larval population was inhibited to settle as compared to the control, while $LC_{50}$ was calculated as the concentration where 50% of the larval population was dead. The experiment was performed in quadruplicate. The experiment results of the inhibitory effect of the four Compounds 1-4 on larvae settlement of *H. elegans* were shown in FIGS. 3, 6, 9, and 12, respectively.

The results showed that the compounds had significant inhibitory activities against larvae of *H. elegans* except for guineensine (Table 5), among which piperoleine B and piperine had stronger inhibitory activities than piperdardine. The $LC_{50}/EC_{50}$ ratios of piperoleine B, piperine and piperdardine were higher than 10 in the bioassay against this species, which indicated that they are non-toxic or low-toxic antifouling compounds.

TABLE 5 the inhibitory effect of piperoleine B, piperine, piperdardine and guineensine on larval settlement of *H. elegans*.

| No. | Sample Name | $EC_{50}$ (μg/ml) | $LC_{50}$ (μg/ml) | $LC_{50}/EC_{50}$ |
|---|---|---|---|---|
| 1 | piperoleine B | 1.0 ± 0.4 | >50 | >49.5 |
| 2 | piperine | 1.3 ± 0.8 | >50 | >38.5 |
| 3 | piperdardine | 7.3 ± 1.6 | >100 | >13.7 |
| 4 | guineensine | >20.0 | >100 | — | n = 4, p < 0.01

Example 6

The Anti-Settlement Activity of the Aforementioned Amide Compounds (1-4) were Evaluated by Inhibitory Assay Using the Competent Larvae of *B. neritina*

The four amide compounds were tested for their abilities to inhibit larvae settlement of *B. neritina*, using an experimental model of inhibition of larvae settlement of *B. neritina* (Xu Y., He H. P., Qian P. Y, et al. Potent antifouling compounds produced by marine streptomyces. *Bioresource Technology*. 2010, 101(4): 1331-1336). Adult *B. neritina* were also collected from Yung Shue O, Hong Kong (22° 25'N, 114° 16'E). The larvae were collected according to the method described by Dobretsov et al. (Dobretsov S., Xiong H. R., Xu Y., Levin L. A., Qian P. Y. Novel antifoulants: inhibition of larval attachment by proteases. *Mar. Biotechnol.* 2007, 9, 388-397). Adult *B. neritina* colonies were placed in a 12 L tank filled with 8 L filtered seawater under a bright artificial light for 1 h to induce the release of their photo-tactic larvae that were able to shortly attach and metamorphose. The actively swimming larvae were collected and added to the test solutions contain different concentrations of samples in 24-well plates at about fifteen (15±3) larvae per well. They were then incubated in the dark at room temperature for 24 h before counting the number of attached and unattached larvae under a dissecting microscope. The $EC_{50}$ was calculated as the concentration where 50% of the larval population was inhibited to settle as compared to the control, while $LC_{50}$ was calculated as the concentration where 50% of the larval population was dead. The experiment was performed in quadruplicate. The experiment results of the inhibitory effect of the four Compounds 1-4 on larvae settlement of the *B. neritina* were shown in FIGS. 4, 7, 10, and 13, respectively.

The results showed that the four amides all had significant inhibitory activities against larvae of *B. neritina* (Table 6), among which piperoleine B and piperine had stronger inhibitory activities against larvae of the fouling organism than the other two. These four amides were non-toxic or low-toxic antifouling compounds according to their $LC_{50}/EC_{50}$ values of higher than 10 in the bioassay against this species.

TABLE 6 the inhibitory effect of piperoleine B, piperine, piperdardine and guineensine on larval settlement of *B. neritina*.

| No. | Sample Name | $EC_{50}$ (μg/ml) | $LC_{50}$ (μg/ml) | $LC_{50}/EC_{50}$ |
|---|---|---|---|---|
| 1 | piperoleine B | 0.7 ± 0.2 | >10 | >14.7 |
| 2 | piperine | 1.6 ± 0.7 | >50 | >30.3 |
| 3 | piperdardine | 8.5 ± 2.1 | >100 | >11.7 |
| 4 | guineensine | 5.7 ± 1.5 | >100 | >17.6 | n = 4, p < 0.01

Example 7

Preparation of Antifouling Coatings

Components with antifouling bioactivities mentioned in the invention were chosen to prepare the antifouling coatings using the known coating technology. For example, these bioactive components were incorporated or diffused into film-forming natural resin, vinyl chloride-vinyl acetate copolymer, and other hydrolysable, soluble or insoluble resins to get the antifouling coatings. These antifouling coatings should release adequate quantities of bioactive components to prevent biofouling on the surface of an object submerged in the water.

While this invention has been described fully and completely with special emphasis upon the preferred embodiments, it should be understood that within the scope of the appended claims the invention may be practiced otherwise than as specifically described herein.

What is claimed is:

1. An antifouling coating, for reducing settlement and/or fouling of marine fouling organisms on a surface of a submerged object, consisting essentially of film-forming components and antifouling components; wherein the film-forming components are selected from the group consisting of glyptal resin, acrylic resin, chlorinated rubber resin, epoxy resin, silicone resin, polyester resin, polyurethane resin, and fluoropolymer resin; and wherein the antifouling components are extracted from *Piper betel* or *Piper szemaoense*.

* * * * *